United States Patent
Woo et al.

(10) Patent No.: US 9,872,976 B2
(45) Date of Patent: Jan. 23, 2018

(54) ASSEMBLY AND METHOD FOR STABILIZING A PERCUTANEOUS CABLE

(75) Inventors: Yi-Ren Woo, Livermore, CA (US); Steven H. Reichenbach, Pleasanton, CA (US); Stephen Briana, Pleasanton, CA (US); Kelly Walsh, Stoneham, MA (US); Kevin Bourque, Reading, MA (US)

(73) Assignee: THORATEC CORPORATION, Pleasanton, CA (US)

(*) Notice: Subject to any disclaimer, the term of this patent is extended or adjusted under 35 U.S.C. 154(b) by 885 days.

(21) Appl. No.: 13/213,571

(22) Filed: Aug. 19, 2011

(65) Prior Publication Data
US 2012/0046515 A1    Feb. 23, 2012

Related U.S. Application Data

(60) Provisional application No. 61/375,766, filed on Aug. 20, 2010.

(51) Int. Cl.
*A61M 1/10* (2006.01)
*A61M 39/02* (2006.01)

(52) U.S. Cl.
CPC .... *A61M 39/0247* (2013.01); *A61M 39/0208* (2013.01); *A61M 2039/0223* (2013.01); *A61M 2039/0261* (2013.01)

(58) Field of Classification Search
CPC ............ A61F 2/0063; A61F 2002/0068; A61F 2002/011; A61F 2/962; A61B 17/122;
(Continued)

(56) References Cited

U.S. PATENT DOCUMENTS 3,834,380 A    9/1974  Boyd
4,041,936 A    8/1977  Carden
(Continued)

FOREIGN PATENT DOCUMENTS

CA    2237203    3/1998
DE     831757    7/1952
(Continued)

OTHER PUBLICATIONS

International Search Report and Written Opinion for PCT/US2011/048381, dated Nov. 18, 2011, 4 pgs.
(Continued)

*Primary Examiner* — Brian Pellegrino
(74) *Attorney, Agent, or Firm* — Squire Patton Boggs (US) LLP

(57) ABSTRACT

A percutaneous cable is attached to a mechanical cardiac pump and is passed through the skin. Sutures can be used to stabilize the cable against movement to prevent disturbing tissue surrounding cable and thereby reduce the incidence of infection. A funnel-shaped tubular device can be used where the cable exits the skin to allow the cable to flex below or near the skin surface as may be desired to accommodate physical activity of a patient. An anchor can be attached to the cable and implanted below the skin surface to stabilize the cable against movement. The anchor can include any one or a combination of a flat mesh material, a bundle of ultrafine filaments, and a barbed filament.

18 Claims, 13 Drawing Sheets

(58) Field of Classification Search
CPC . A61B 17/064; A61B 17/11; A61B 2562/225;
A61B 2017/1132; A61B 2017/00336;
A61B 2017/00867; A61N 1/0492; A61N
1/0456; A61N 1/057; A61M 39/0208;
A61M 39/0247; A61M 1/10; A61M
2001/1633; A61M 1/127
USPC .......................................... 606/153; 623/1.36
See application file for complete search history.

(56) References Cited

U.S. PATENT DOCUMENTS

| | | | |
|---|---|---|---|
| 4,366,819 A * | 1/1983 | Kaster | 606/153 |
| 4,368,736 A * | 1/1983 | Kaster | 606/153 |
| 4,416,664 A | 11/1983 | Womack | |
| 4,480,639 A | 11/1984 | Peterson et al. | |
| 4,553,814 A * | 11/1985 | Bahl et al. | 385/86 |
| 4,579,120 A * | 4/1986 | MacGregor | 600/392 |
| 4,906,233 A | 3/1990 | Morjtjchi et al. | |
| 5,084,026 A | 1/1992 | Shapiro | |
| 5,144,848 A | 9/1992 | Uenishi et al. | |
| 5,163,960 A * | 11/1992 | Bonutti | 128/898 |
| 5,167,229 A | 12/1992 | Peckham et al. | |
| 5,211,546 A | 5/1993 | Isaacson et al. | |
| 5,211,573 A | 5/1993 | Cross | |
| 5,224,935 A | 7/1993 | Hollands | |
| 5,237,988 A | 8/1993 | McNeese | |
| 5,254,133 A * | 10/1993 | Seid | 606/151 |
| 5,289,821 A | 3/1994 | Schwartz | |
| 5,356,432 A * | 10/1994 | Rutkow | A61F 2/0063 623/23.72 |
| 5,370,509 A | 12/1994 | Golding et al. | |
| 5,376,108 A | 12/1994 | Collins et al. | |
| 5,413,562 A | 5/1995 | Swauger | |
| 5,443,060 A | 8/1995 | Visveshwara et al. | |
| 5,443,065 A | 8/1995 | Berghoff et al. | |
| 5,681,290 A | 10/1997 | Alexander | |
| 5,695,471 A | 12/1997 | Wampler | |
| 5,810,781 A | 9/1998 | Bierman | |
| 5,824,073 A * | 10/1998 | Peyman | 623/4.1 |
| 5,840,070 A | 11/1998 | Wampler | |
| 5,849,033 A | 12/1998 | Mehmanesh et al. | |
| 5,876,234 A | 3/1999 | Hester | |
| 5,904,646 A | 5/1999 | Jarvik | |
| 5,916,199 A | 6/1999 | Miles | |
| D495,619 S | 5/2000 | Bierman | |
| 6,066,086 A | 5/2000 | Antaki et al. | |
| 6,071,093 A | 6/2000 | Hart | |
| 6,080,133 A | 6/2000 | Wampler | |
| 6,100,618 A | 8/2000 | Schoeb et al. | |
| 6,117,086 A | 9/2000 | Shulze | |
| 6,120,537 A | 9/2000 | Wampler | |
| 6,158,984 A | 12/2000 | Cao et al. | |
| 6,217,541 B1 | 4/2001 | Yu | |
| 6,227,797 B1 | 5/2001 | Watterson et al. | |
| 6,234,772 B1 | 5/2001 | Wampler et al. | |
| 6,234,998 B1 | 5/2001 | Wampler | |
| 6,264,635 B1 | 7/2001 | Wampler et al. | |
| 6,324,415 B1 | 11/2001 | Spehr et al. | |
| 6,368,083 B1 | 4/2002 | Wampler | |
| 6,379,816 B1 | 4/2002 | De Loose et al. | |
| 6,447,485 B2 | 9/2002 | Bierman | |
| 6,497,650 B1 * | 12/2002 | Nicolo | 600/37 |
| 6,542,781 B1 | 4/2003 | Koblish et al. | |
| 6,606,522 B2 | 8/2003 | Schell | |
| 6,623,420 B2 | 9/2003 | Reich et al. | |
| 6,650,921 B2 | 11/2003 | Spehr et al. | |
| 6,688,861 B2 | 2/2004 | Wampler | |
| 6,689,104 B2 | 2/2004 | Bierman | |
| 6,837,875 B1 | 1/2005 | Bierman | |
| 7,284,729 B2 | 10/2007 | Walsh et al. | |
| 2001/0009645 A1 | 7/2001 | Noda | |
| 2002/0068848 A1 | 6/2002 | Zadini et al. | |
| 2002/0165493 A1 | 11/2002 | Bierman | |
| 2002/0183628 A1 | 12/2002 | Reich et al. | |
| 2003/0028148 A1 | 2/2003 | Hampton et al. | |
| 2003/0109770 A1 | 6/2003 | Sharkey et al. | |
| 2004/0084398 A1 | 5/2004 | Breitschwerdt et al. | |
| 2004/0084399 A1 | 5/2004 | Cook et al. | |
| 2004/0186542 A1 | 9/2004 | van Venrooij et al. | |
| 2004/0199122 A1 | 10/2004 | Bierman et al. | |
| 2004/0234397 A1 | 11/2004 | Wampler | |
| 2005/0085118 A1 | 4/2005 | Robbins et al. | |
| 2007/0129779 A1 | 6/2007 | Ayre et al. | |
| 2007/0161847 A1 * | 7/2007 | Woodard et al. | 600/16 |
| 2007/0191884 A1 * | 8/2007 | Eskridge | A61B 17/12113 606/213 |
| 2007/0231135 A1 | 10/2007 | Wampler et al. | |
| 2008/0080983 A1 | 4/2008 | Wampler et al. | |
| 2008/0085184 A1 | 4/2008 | Wampler et al. | |
| 2008/0089779 A1 | 4/2008 | Wampler et al. | |
| 2008/0089797 A1 | 4/2008 | Wampler et al. | |
| 2008/0183257 A1 * | 7/2008 | Imran et al. | 607/117 |
| 2010/0133099 A1 * | 6/2010 | Norgaard et al. | 204/403.01 |

FOREIGN PATENT DOCUMENTS

| | | |
|---|---|---|
| EP | 0 022 370 | 1/1981 |
| EP | 122089 | 10/1984 |
| EP | 0356683 | 3/1990 |
| EP | 0 367 354 | 5/1990 |
| EP | 1 354 606 | 10/2003 |
| EP | 1475123 | 11/2004 |
| EP | 1 632 201 | 3/2006 |
| JP | 10309321 | 11/1998 |
| JP | 2002-224066 | 8/2002 |
| JP | 2004-278375 | 10/2004 |
| WO | WO 87/06122 | 10/1987 |
| WO | WO 89/10727 | 11/1989 |
| WO | WO 97/29795 | 8/1997 |
| WO | WO 2001/05023 | 1/2001 |
| WO | WO 2003/063952 | 8/2003 |
| WO | WO 2004/091432 | 10/2004 |
| WO | WO 2005/075017 | 8/2005 |
| WO | WO 2007/006080 | 1/2007 |
| WO | WO 2010/025411 | 3/2010 |

OTHER PUBLICATIONS

International Search Report for PCT/AU2006/000953, dated Aug. 17, 2006. 4 pgs.
International Search Report and Written Opinion for PCT/AU2005/000135, dated Mar. 18, 2005, 4 pgs.

* cited by examiner

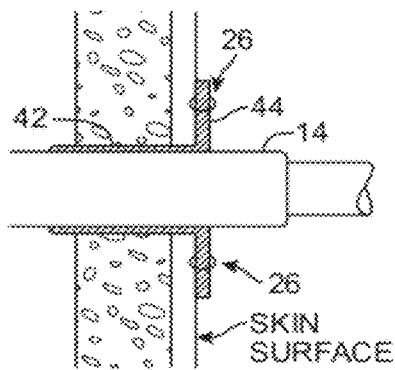
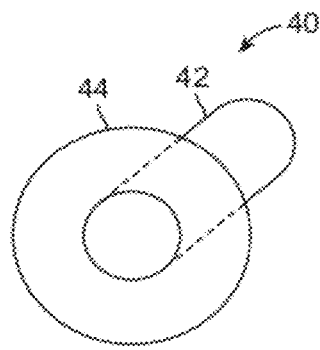
FIG. 5A  FIG. 5B
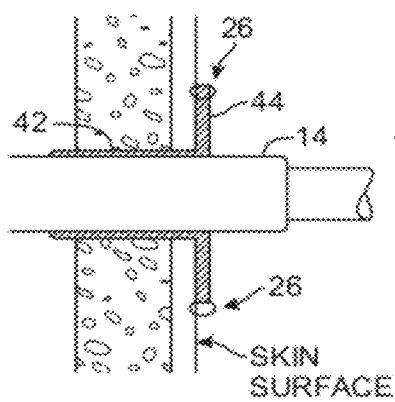
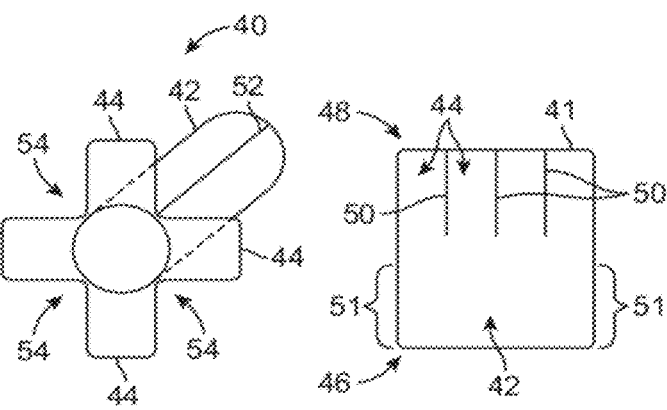
FIG. 6A  FIG. 6B  FIG. 6C
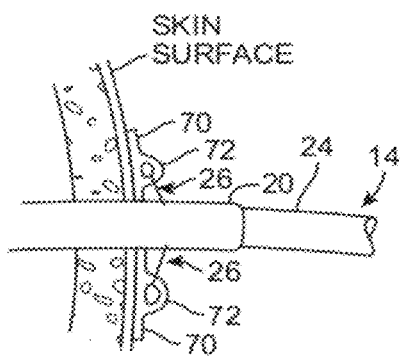
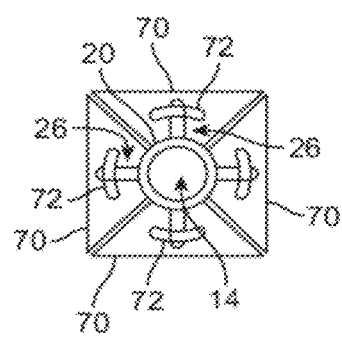
FIG. 7A  FIG. 7B

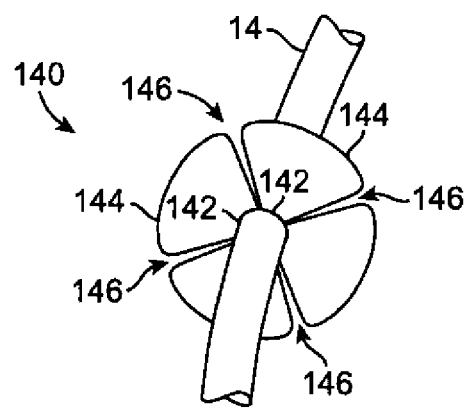 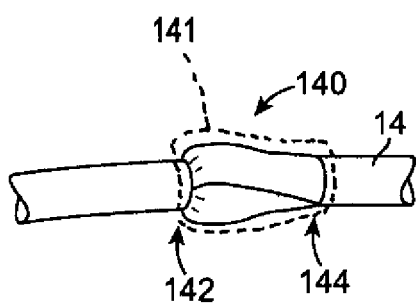
FIG. 14A  FIG. 14B
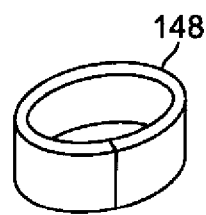 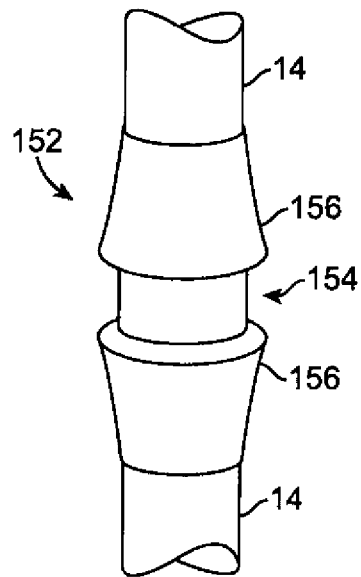
FIG. 15A  FIG. 15B

ASSEMBLY AND METHOD FOR STABILIZING A PERCUTANEOUS CABLE

CROSS-REFERENCE TO RELATED APPLICATION

This application claims the benefit of U.S. Provisional Application No. 61/375,766, filed Aug. 20, 2010, which is incorporated herein by reference.

FIELD OF THE INVENTION

This invention relates to medical implants and, more particularly, to an assembly and method for stabilizing a percutaneous cable against movement.

BACKGROUND OF THE INVENTION

Various diagnostic or therapeutic medical devices that have been and are currently in development, such as artificial hearts and ventricular assist devices, are implanted within the human body and, due to their substantial functionality, require connection to a power source and/or controller located outside the body. A percutaneous lead or cable connects the implanted medical device to the external power source and/or controller. Because the percutaneous cable passes through the skin, precautions must be taken to prevent infection and injury to tissue around the exit site. Conventional precautions include the use of antimicrobial agents and use of an external clip to prevent movement of a segment of percutaneous cable near the exit site. Many conventional clips are designed to be located at some short distance away from the exit site, which still allows the percutaneous cable to pull away from surrounding tissue, even if by a small distance. This occurs because normal physical activity by the subject causes clothing and other objects in the environment to push or otherwise agitate the tissue and/or cable segment immediately adjacent the exit site. Abdominal binders, patches, and belts have also been used but these devices are often difficult to use properly, restrict movement of the patient, have low patient compliance associated with them, or even if used properly allow some relative movement between cable and tissue. Movement, even by small amounts, slows healing of the exit wound, results in re-injury, and/or produces an interfacial gap for pathogen entry.

Although percutaneous cable infection rates have been reduced over the years, the risk of infection remains a substantial source of patient morbidity and mortality, and there is a continuing need to reduce such risk. What is needed is an assembly and method that further limits or prevents a percutaneous cable from pulling away from surrounding tissue, even by small distances, so as to promote wound healing, prevent re-injury, prevent the occurrence of interfacial gaps, and thereby reduce the incidence of infection.

SUMMARY OF THE INVENTION

Briefly and in general terms, the present invention is directed to a medical assembly and method for stabilizing a percutaneous cable.

In aspects of the present invention, an assembly comprises a percutaneous cable and an anchor attached to the percutaneous cable. The anchor extends radially away from the percutaneous cable, and is configured to engage biological tissue by tissue growth in the anchor or by barbs on the anchor.

In aspects of the present invention, a method comprises passing a percutaneous cable through a skin of a human or animal body, and positioning an anchor within biological tissue below an outer surface of the skin. The anchor is attached to the percutaneous cable, extends radially away from the percutaneous cable, and is configured to engage biological tissue by tissue growth in the anchor or by barbs on the anchor.

In aspects of the present invention, a subdermal anchor comprises a structure configured to engage biological tissue by tissue ingrowth or hooks into the tissue. The structure is selected from the group consisting of a bundle of filaments wherein the filaments are attached together, a flat mesh, and a plurality of barbed filaments.

In aspects of the present invention, an assembly comprises a percutaneous cable and a securement. The percutaneous cable comprises a covering. The securement is attached to the covering and is configured to stabilize the percutaneous cable relative to biological tissue.

In detailed aspects, the securement is a suture sewn through the covering. In other aspects the securement comprises a flexible tubular device, the percutaneous cable passes through the flexible tubular device, the flexible tubular device comprises a first opening and a second opening larger than the first opening, the first opening sized to engage the percutaneous cable, the second opening sized to allow radial movement of the percutaneous cable relative to the second opening. In further aspects, the flexible tubular device has a conical wall that tapers down in diameter from the second opening toward the first opening. In still further aspects, the flexible tubular device comprises a cylindrical wall disposed between the conical wall and the first opening, the cylindrical wall configured to engage the percutaneous cable. In other further aspects, a porous layer is on an outer surface of the flexible tubular device, the porous layer configured to allow tissue growth in the porous layer. In other aspects, the securement comprises a subdermal anchor protruding radially outward from the percutaneous cable. In further aspects, the subdermal anchor comprises a bundle of polyester filaments, the bundle having a fixed end and a free end, the fixed end attached to the percutaneous cable, the polyester filaments attached together at the fixed end. In other further aspects, the subdermal anchor comprises a flat mesh. In other aspects, the assembly further comprises a mechanical cardiac pump connected to the percutaneous cable.

In some aspects of the present invention, an assembly comprises a percutaneous cable, tubular device, and a securement feature. The tubular device comprises a first tube segment and a second tube segment, the percutaneous cable passing through the first and second tube segments, the percutaneous cable engaged to the first tube segment and disengaged from the second tube segment. The securement feature is disposed on an outer surface of the tubular device, the securement feature configured to stabilize the tubular device relative to biological tissue.

In detailed aspects, the securement feature is a fabric configured to allow ingrowth of biological tissue. In other detailed aspects, the second tube segment is collapsible. In further aspects, the second tube segment is made of a silicone material. In other further aspects, the second tube segment has a conical wall having a cross-dimension that enlarges from the first tube segment toward an opening of the second tube segment, and the percutaneous cable is movable in a radial direction relative to the conical wall.

In aspects of the present invention, a method comprises passing a percutaneous cable through a skin of a human or animal body, and placing a suture through the skin and through a fabric covering attached to the percutaneous cable.

In detailed aspects, the fabric covering is a fabric or porous material. In more detailed aspects, the fabric allows for growth of biological tissue of the human or animal body into the fabric. The fabric can be knitted or weaved. In other detailed aspects, the suture is configured to resorb into the human or animal body.

In aspects of the present invention, a method comprises passing a percutaneous cable through a skin of a human or animal body, and positioning a tubular device in contact with biological tissue at or adjacent to the skin. The tubular device comprises a first tube segment and a second tube segment, the percutaneous cable passing through the first and second tube segments, the percutaneous cable engaged to the first tube segment and disengaged from the second tube segment.

In other aspects, a knitted fabric attached to the tubular device allows for growth of biological tissue of the human or animal body into the knitted fabric. In still other aspects, the passing of the percutaneous cable through the skin comprises inserting an end of the percutaneous cable from below the skin and out from an outer surface of the skin. In further aspects, the positioning of the tubular device comprises collapsing the second tube segment, followed by inserting an opening of the second tube segment from below the skin into the biological tissue until the opening is adjacent to the skin surface, followed by allowing the second tube segment to expand. In other aspects, the passing of the percutaneous cable through the skin comprises inserting an end of the percutaneous cable into an outer surface of the skin and out from below the skin. In other aspects, the positioning of the tubular device comprises sliding the first tube segment on the percutaneous cable and into the biological tissue until an opening of the second tube segment is adjacent to the skin surface. In still other aspects, the method further comprises allowing the percutaneous cable to bend within a volume surrounded by the second tube segment.

The features and advantages of the invention will be more readily understood from the following detailed description which should be read in conjunction with the accompanying drawings.

BRIEF DESCRIPTION OF THE DRAWINGS

FIGS. 5A and 5B are sectional and perspective views of a sleeve, respectively, showing a tube portion that can be attached to an outer covering of a percutaneous cable and a flange portion that can lie flat on top of the surface of the skin.

FIGS. 6A-6C are sectional, perspective, and plan views, respectively, showing a tube portion that can be attached to an outer covering of a percutaneous cable and showing multiple flanges formed from a single piece of rectangular material.

FIGS. 7A and 7B are plan and sectional views of an exit site, respectively, showing base pieces bonded to the surface of the skin and holding sutures connected to a percutaneous cable.

FIGS. 14A and 14B are perspective views of a subdermal anchor in the form of a mesh skirt attached to a percutaneous cable, the skirt having four slits.

FIGS. 15A and 15B are perspective views showing a ring for a subdermal anchor and showing a receptacle for retaining the ring on a percutaneous cable.

DETAILED DESCRIPTION OF THE INVENTION

Figure 1:
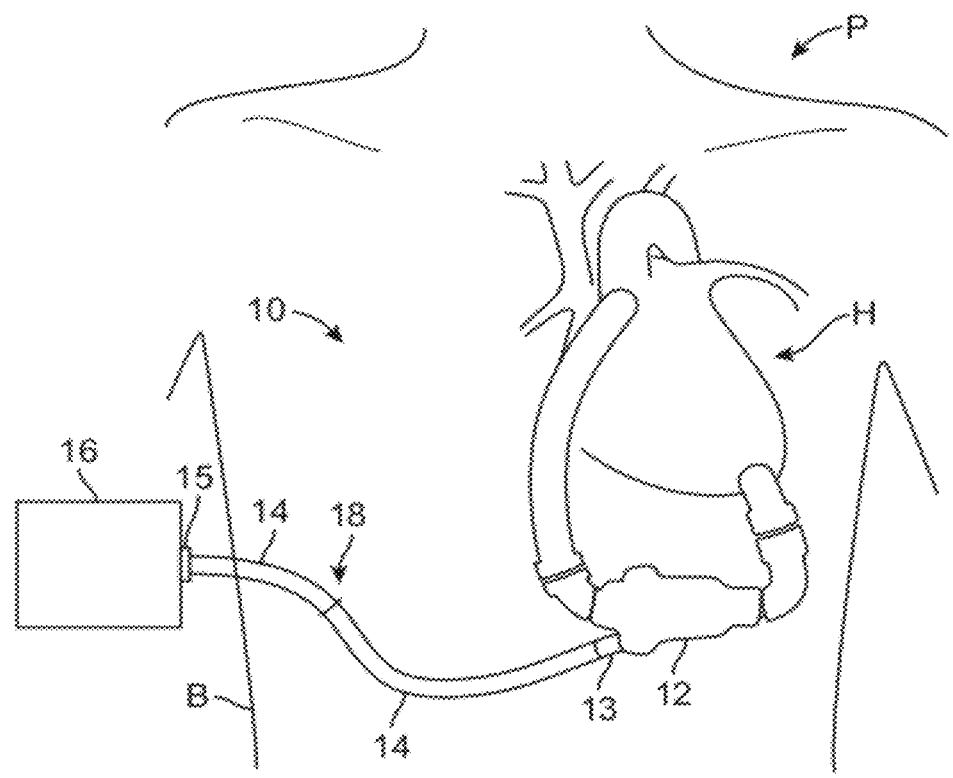
FIG. 1 is a diagram of a medical assist assembly, showing a percutaneous cable connecting an internal device within a patient's body to an external device outside the patient's body.

The word "percutaneous" as used herein means through the skin and can refer to access to an internal anatomical body part through a small puncture through the skin, and when used to describe a structure means that the structure passes through or is configured to pass through the skin.

The word "subdermal" means below the skin surface, and when used to describe a structure means that the structure is below the skin surface or is configured for placement below the skin surface.

The word "biocompatible" when used to describe a polymer means that the polymer in its intact, as synthesized state, and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

The words "bioabsorbable" and "biodegradable" are used interchangeably herein and refer to materials that are capable of being degraded or absorbed when exposed to bodily fluids such as blood, and components thereof such as enzymes, and that can be gradually resorbed, absorbed, and/or eliminated by a human or animal body.

The words "substantial" and "substantially" when used herein to describe a condition means that the condition is present in absolute or perfect form, as well as in a form that is not necessarily absolute or perfect but would be considered close enough to those of ordinary skill in the art to warrant designating the condition as still being present.

The word "distal" is used herein to describe a structure that, unless the context shows otherwise, is oriented away from a patient, or is located further away from the patient as compared to a structural element that would otherwise be described as proximal.

The term "in vivo" as used herein to describe a structure means that the structure is within a human or animal body or is configured to be located within the body after a surgical procedure is completed.

The term "ex vivo" as used herein to describe a structure means that the structure is outside a human or animal body or is configured to be located outside the body after a surgical procedure is completed.

The word "lumen" as used herein refers to a through hole or a tubular passageway.

The words "axial" and "longitudinal" relate to a direction, line, or orientation that is substantially parallel to a central axis of a cylindrical or tubular structure, unless the context shows otherwise.

The words "radial" and "radially" relate to a direction, line or orientation that radiates away from a center point or that is substantially perpendicular to a central axis of a cylindrical or tubular structure, unless the context shows otherwise.

The word "circumferential" relates to a direction along a circumference of a circular, cylindrical, or tubular structure.

The word "oblique" as used herein relates to an angle or orientation that is neither substantially perpendicular nor substantially parallel in relation to a referenced structure.

Referring now in more detail to the exemplary drawings for purposes of illustrating embodiments of the invention, wherein like reference numerals designate corresponding or like elements among the several views, there is shown in FIG. 1 a therapeutic medical assembly 10, in situ, to assist or enhance a body function of a patient P. The medical device assembly 10 comprises a mechanical cardiac pump 12 implanted within the chest cavity of the patient and connected to the biological heart H of the patient. The mechanical cardiac pump is a left ventricular assist device (VAD) connected to the left ventricle of the heart. A percutaneous cable 14, also referred to as a percutaneous lead, is connected to the mechanical cardiac pump and extends from within the body of the patient, through an exit wound through the abdominal wall of the patient, and to an external device 16 located outside the patient's body B. The general region where the percutaneous cable exits the patient's body is referred to as an exit site 18.

The external device 16 comprises a power source and an electronic controller. The percutaneous cable comprises power lines and communication lines. The power lines are metal wires that deliver electrical power to the mechanical cardiac pump from the power source, which can be a battery. The communication lines can be in the form of metal wires or optical filaments that provide unidirectional or bidirectional data communication, in the form of electrical or optical signals, with the electronic controller.

The percutaneous cable 14 comprises an in vivo connector 13 and an ex vivo connector 15. The in vivo connector 13 is located at the in vivo end of the percutaneous cable and is configured to allow the percutaneous cable to be selectively connected and disconnected from the mechanical cardiac pump 12. The ex vivo connector 15 is located at the ex vivo end of the percutaneous cable and is configured to allow the percutaneous cable to be selectively connected and disconnected from the external device 16. In other embodiments, a percutaneous cable comprises only one of the connectors 13, 15 since only one connector is sufficient to allow the percutaneous cable to be fed through an exit site.

The in vivo connector 13 allows the mechanical cardiac pump 12 without the percutaneous cable 14 to be placed through an opening to the chest cavity of the patient (the opening larger than an exit site). After the mechanical cardiac pump is placed in the patient, the in vivo connector 13 is inserted from outside the patient into an exit site (located a distance away from the chest cavity opening) and pulled to the mechanical cardiac pump via a "tunneling" procedure. Next, the in vivo connector is mechanically actuated, such as by a twist lock mechanism, clip mechanism and/or methods known to one of ordinary skill in the art, so as to form a substantially fluid-tight seal that fastens the percutaneous cable to a corresponding connector on the mechanical cardiac pump. The in vivo connector 13 and the corresponding connector on the mechanical cardiac pump comprise electrical leads that mate with each other.

The ex vivo connector 15 allows for a different implantation procedure. The mechanical cardiac pump 12, with the percutaneous cable attached, is placed through an opening to the chest cavity of the patient. Next, a "tunneling" procedure is performed in which the ex vivo connector 15 inside the patient's chest cavity is pushed out of an exit site (located a distance away from the chest cavity opening). Later, the ex vivo connector is mechanically actuated, such as by a twist lock mechanism, clip mechanism and/or methods known to one of ordinary skill in the art, so as to form a substantially fluid-tight seal that fastens the percutaneous cable to a corresponding connector on the external device 16. The ex vivo connector 15 and the corresponding connector on the external device comprise electrical leads that mate with each other.

Figure 2:
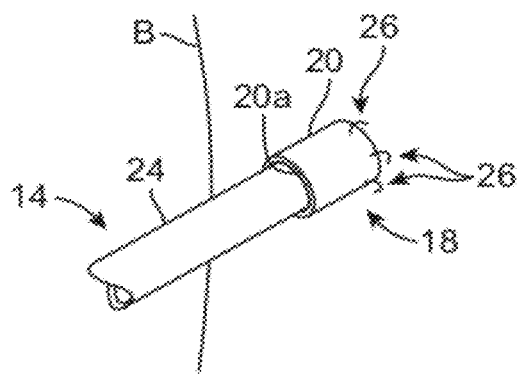
FIG. 2 is perspective view of a percutaneous cable at an exit site on a patient's body, showing sutures securing the percutaneous cable to the patient's skin.
Figure 3:
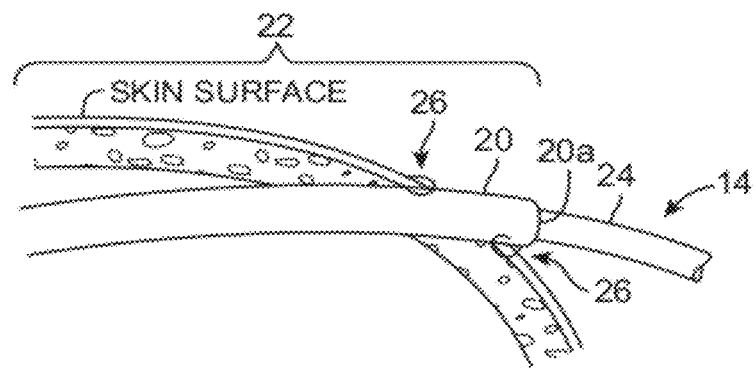
FIG. 3 is sectional view of the percutaneous cable of FIG. 2, showing the sutures attached to an outer covering of the percutaneous cable.

As shown in FIGS. 2 and 3, the external surface of the percutaneous cable 14 comprises a tubular outer covering 20 that is permeable to fluids, porous and configured to allow ingrowth of the patient's biological tissue that contacts the covering. Tissue ingrowth includes tissue adhesion to and encapsulation of the covering. Tissue ingrowth helps to stabilize the percutaneous cable from movement relative the skin and other parts of the patient's anatomy. As such, the outer covering functions as a securement of the percutaneous cable in addition to sutures (as described below).

The outer covering 20 surrounds a segment 22 of the percutaneous cable that extends from within the patient, through the skin, and outside the patient. Beneath the outer covering is a polymer layer 24 of the percutaneous cable. The polymer layer is substantially impermeable to fluids. A silicone adhesive is optionally used to fasten the outer covering to the polymer layer. The polymer layer encases power and communication lines of the percutaneous cable and extends out beyond the ex vivo end 20a of the outer covering. The outer covering is a fabric, such as a textile made of polymer fibers including but not limited to DACRON® fibers and other polyester fibers. The polymer fabric, which may be knitted, can be in the form of velour.

As shown in FIGS. 2 and 3, sutures 26 are used as additional securement for the percutaneous cable 14. The sutures 26 extend as loops into the outer covering 20 and into the skin of the patient. In particular, each suture penetrates through the outer covering 20, into the skin, and loops back out through the skin where opposite ends of the suture are tied together in a knot. Preferably though not necessarily, the sutures do not penetrate the fluid-impermeable polymer layer 24 beneath the outer covering 20. The sutures are spaced apart from each other at substantially equal distances to evenly distribute forces that would tend to move the percutaneous cable out of or away from the skin. The sutures can be bioabsorbable or non-bioabsorbable. The sutures can be a synthetic polymer monofilament or made of any material known in the art for surgical sutures.

In use, the percutaneous cable 14 is pushed into or pulled out of an exit wound in the skin so that a desired length of the percutaneous cable is in the patient. The length within the patient must be sufficient to reach the mechanical cardiac pump 12 (FIG. 1). After the percutaneous cable is in the desired position relative to the skin, sutures 26 are sewn with a curved needle through the outer covering 20 and the skin. It is contemplated that a series of six to eight sutures are placed. In addition to limiting relative movement between the cable and tissue, the sutures will close any mismatch in the size of the exit site 18 and the cable.

Figure 4:
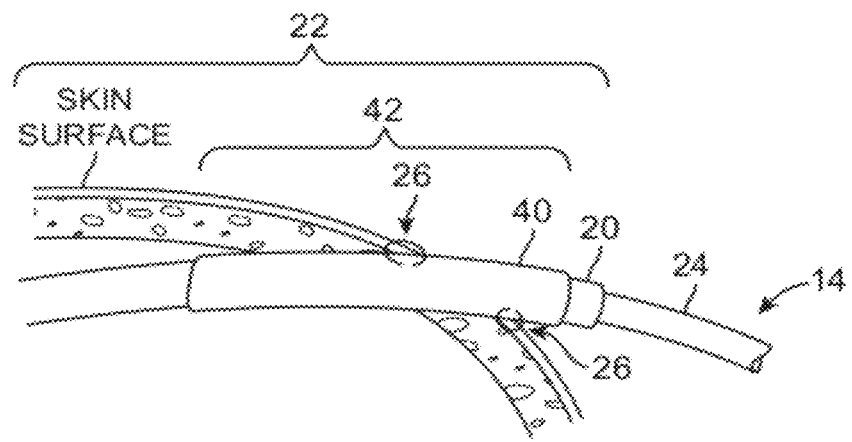
FIG. 4 is a sectional view of a percutaneous cable, showing a sleeve on an outer covering of the percutaneous cable and showing sutures connecting the sleeve to skin.

Referring now to FIG. 4, another embodiment comprises a percutaneous cable 14 having a tubular sleeve 40 located at the exit site. The sleeve helps avoid puncturing or otherwise damaging an underlying fluid-impermeable polymer layer 24 of the percutaneous cable during the suturing process. The sleeve is disposed on top of an outer covering 20 and thus provides more material for sutures 26 to hook into. The sleeve covers a segment 42 of the percutaneous cable that is shorter than the segment 22 covered by the outer covering. The sleeve is fastened in position on the percutaneous cable by friction fit, heat bonding, and/or adhesive bonding.

The sutures 26 that loop through the sleeve 40 and surrounding skin function as securement for the percutaneous cable 14. The sleeve itself functions as securement in that surrounding tissue that grows into pores of the sleeve helps to stabilize the percutaneous cable against movement. The sleeve is porous and can be made of the same material and have the same construction as the outer covering 20 or it can be made of a different biocompatible material. The sleeve is optionally thicker than the outer covering.

The sutures provide immediate rigid securement during initial placement of the percutaneous cable. Thereafter, over the course of a healing period the porous sleeve becomes the predominant mode of securement, allowing for subsequent suture removal, if that is deemed clinically advantageous.

As shown in FIGS. 5A-6C, other embodiments comprise a sleeve 40 having a tube portion 42 and a flange portion 44 that extends radially outward from the tube portion. When the device is secured in a final position on a patient, the tube portion is located in vivo, within the exit site of the patient, and the flange portion is located ex vivo and lies substantially flat on the surface of the skin. The flange portion is flexible so that during placement of the device, the flange portion can be oriented in-line with the tube portion as opposed to extending radially outward. The in-line orientation facilitates a tunneling procedure in which the flange portion is pushed out from beneath the skin to the skin surface before the flange portion is positioned flush against the skin surface. After the flange portion is positioned flush against the skin surface, sutures 26 can be placed near the middle of the flange portion 44 (FIG. 5A) so that each suture penetrates through a flange portion and the underlying skin, then loops back out through the skin and another flange portion where opposite ends of the suture are tied together in a knot above the flange portion. The sutures can also be placed at an outer perimeter or edge of the flange portion (as illustrated FIG. 6A) to distribute mechanical forces over a larger area and/or over a greater number of sutures. Other configurations and patterns of securing the flange portions using sutures by those with ordinary skills in the art are also possible and will not be exhaustively listed here.

FIGS. 6B-6C illustrate another embodiment of a sleeve similar to that shown in FIGS. 5A-5B for use in securing a percutaneous lead. In FIG. 6C, a sleeve 40 is made from a substantially flat, rectangular piece of material 41, such as knitted polyester fabric, having an in vivo end 46 and an ex vivo end 48. A plurality of slits 50 are formed at the ex vivo end 48. Edges 51 at opposite sides of the in vivo end 46 are joined together, such as by sewing, to form a tube portion 42 of the sleeve. The joined edges form a seam 52 on the tube portion (for example, as illustrated in FIG. 6B). In FIG. 6B, when joining the edges 51, the slits 50 open and allow portions of the material to spread apart to form multiple flange portions 44 of the sleeve. Gaps 54 between the various flange portions 44 allow the flange portions to fold down with minimal or no overlap of material, which facilitates performance of a tunneling procedure in which the flange portions are pushed out from beneath the skin to the skin surface. In the illustrated embodiment there are four flange portions and it will be appreciated that a lesser or greater number of flange portions can be implemented.

As shown in FIGS. 7A and 7B, a base piece 70 can be attached ex vivo on the skin surface surrounding an exit wound. Sutures 26 are secured to a percutaneous cable 14 and are attached to the base piece without penetrating the skin. A biocompatible adhesive, such as used for securing colostomy bags and other moisture-resistant adhesives known in the art for adhering onto skin for extended periods of time, is used to fasten the bottom surface of the base piece to the skin. There is a small loop 72 on the top surface of the base piece. The loop is sized to receive one or more sutures.

In use, a suture 26 penetrates through an outer covering 20 of the percutaneous cable 14 and extends through a loop 72 of the base piece 70 without penetrating the skin. Opposite ends of the suture are tied in a knot above the skin to secure the outer covering 20 to the base piece. In the illustrated embodiment there are four separate base pieces and it will be appreciated that a lesser or greater number of base pieces can be implemented. It will be appreciated that the four base pieces can be combined as one piece with a central hole for the percutaneous cable. It will also be appreciated the sleeve 40 of FIG. 4 can be used in combination with a base piece to provide additional material on the percutaneous cable for sutures to hook into.

Figure 8A:
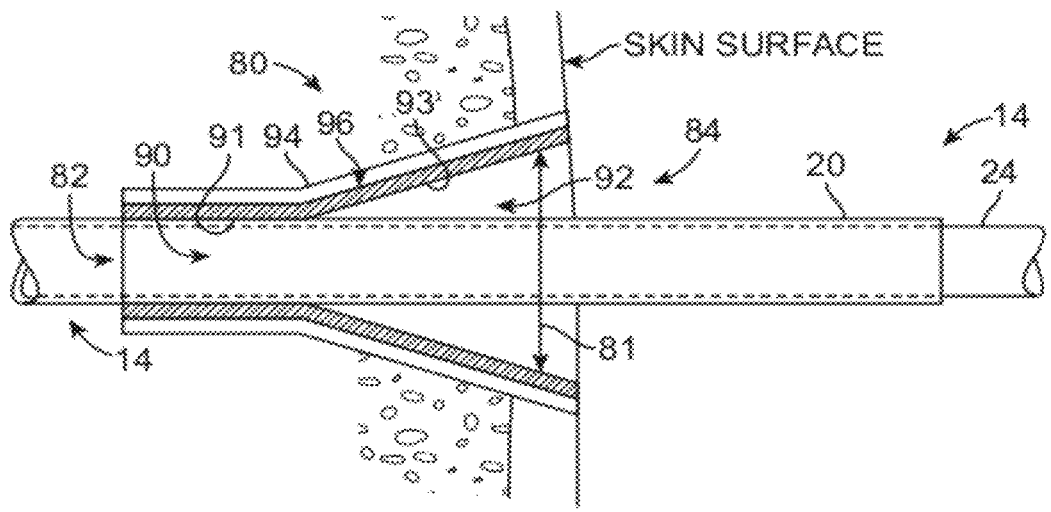
FIGS. 8A and 8B are sectional views of an exit site, showing a tubular device and a percutaneous cable moveable in radial directions within the tubular device.
Figure 8B:
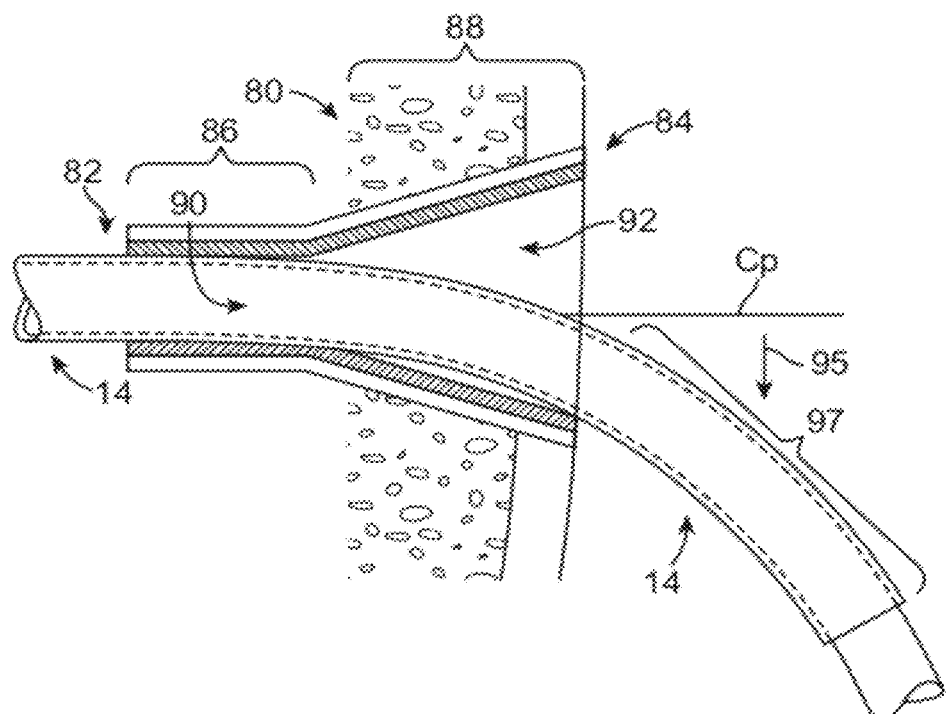

Referring next to FIGS. 8A and 8B, a percutaneous cable 14 can be secured to surrounding tissue at the exit site by a funnel-shaped, tubular device 80 that enables the percutaneous cable to flex beneath and/or near the skin surface without disturbing or injuring surrounding tissue. Such flexing may be desirable to accommodate body movement of the patient relative to an external device to which the percutaneous cable is connected. The tubular device functions as a securement for the percutaneous cable as described below. The percutaneous cable has a fluid-impermeable polymer layer 24 and a fabric outer covering 20. The fabric outer cover 20 is made of the same material and has the same construction as the outer covering in previously described embodiments. The tubular device 80 is disposed on or over the outer covering. It will be appreciated that the segment of the percutaneous cable within the tubular device need not have a fabric outer covering, in which case the tubular device rests directly on and contacts the fluid-impermeable polymer layer of the percutaneous cable.

The percutaneous cable 14 passes through the tubular device 80 so as to extend out of openings at opposite ends of the tubular device. The openings at opposite ends are referred to individually as a first opening 82 and second opening 84. The tubular device 80 comprises a first tube segment 86 and a second tube segment 88. The two segments are connected to each other and the second tube segment 88 is located distally from the first tube segment 86.

The first tube segment 86 has a lumen 90 formed by a cylindrical wall 91 sized to engage the percutaneous cable and has a substantially uniform internal diameter. The cylindrical wall of the first tube segment can be fastened by a friction fit with the underlying segment of the percutaneous cable (for example, a friction fit with the outer covering or impermeable layer of the percutaneous cable). Alternatively or in combination with the friction fit, the cylindrical wall of the first tube segment can be fastened on the percutaneous cable by heat bonding and/or adhesive bonding.

In some embodiments, the percutaneous cable is tightly fastened against the first tube segment 86 such that nothing can penetrate or pass through in between the percutaneous cable 14 and the cylindrical wall 91 (from the second tube segment). The tight fit between the percutaneous cable and the first tube segment 86 helps to distribute force or stress from the cable to tissue surrounding the two tube segments 86, 88 (as explained below).

The second tube segment 88 has a lumen 92 formed by a funnel-shaped wall 93. The second tube lumen is sized greater than the first tube lumen 90. The second tube lumen is also sized greater than the percutaneous cable to allow movement of the percutaneous cable in radial directions. The second opening 84, located at the distal end of the second tube lumen, has an internal diameter that is at least twice the outer diameter of the percutaneous cable. The second tube lumen tapers down in size from the second opening 84 toward the first tube segment 86. Alternatively stated, the second tube lumen flares out in size from the first tube segment to the second opening. The funnel-shaped wall has an internal diameter 81 that allows the percutaneous cable to move in a radial direction independently of the tubular device 80, such as may occur from time to time due to physical activity of the patient. Thus, physical activity is less likely to disturb or injure the exit site. As shown in FIG. 8B, radial movement 95 could cause a segment 97 of the percutaneous cable to be off center or non-aligned with the central axis Cp of the percutaneous cable inside the first tube segment. Even with the radial movement 95, the second tube segment 88 remains secured to the surrounding tissue and the exit site is undisturbed and not injured.

In use, the second opening 84 is substantially flush with the skin surface. Substantially the entire tubular device 80 is beneath the skin surface. Beneath the skin surface there is a porous layer 94 of material attached on top of a radially outward facing surface 96 of the tubular device 80. The entire outward facing surface is covered by the porous layer. The outward facing surface is a substrate on which the porous layer is bonded with adhesive and/or applied heat energy. The porous layer is configured to allow ingrowth of biological tissue that contacts it. The porous layer functions as a securement in that tissue ingrowth over time helps to secure the tubular device against the skin and thus stabilize the percutaneous cable 14 against movements relative to the skin. The porous layer of material can be the same material and have the same construction used for the outer covering 20.

The cylindrical wall 91 and the funnel-shaped wall 93 of the tubular device 80 are substantially fluid-impermeable and are made of a flexible, semi-rigid material, such as cured silicone having a rubber-like elasticity and resiliency. The funnel-shaped wall 93 can be collapsed and/or folded during a tunneling procedure in which the second opening 84 is pushed out from beneath the skin through an exit wound. Although flexible, the funnel-shaped wall 93 has sufficient resiliency to self-expand from its collapsed configuration to an expanded configuration (shown in FIGS. 8A and 8B) and has sufficient rigidity after expansion to keep surrounding biological tissue from collapsing the second tube lumen 92. The funnel-shaped wall 93 maintains a funnel-shaped opening in the biological tissue at the exit site.

In some embodiments, the first tube segment 86 is configured to slide axially on the percutaneous cable 14. For example, a "reverse" tunneling procedure can be performed in which an in vivo end of the percutaneous cable is inserted from outside the patient's body into and through an exit wound. After a desired length of the percutaneous cable has been pulled and/or pushed into the patient, the tubular device 80 outside of the patient can be slid down on the percutaneous cable until the first and second tube segments 86 and 88 are inside the exit wound and the edge of the second opening 84 is substantially flush with the skin surface.

In the illustrated embodiments of FIGS. 8A and 8B, the tubular device 80 is substantially symmetrical in all radial directions. The second tube segment 88 is cone-shaped with a conical wall that forms the second tube lumen 92. Also, the edge of the second opening 92 forms a circle so as to allow some flexing of the percutaneous cable 14 in all radial directions.

Figure 9A:
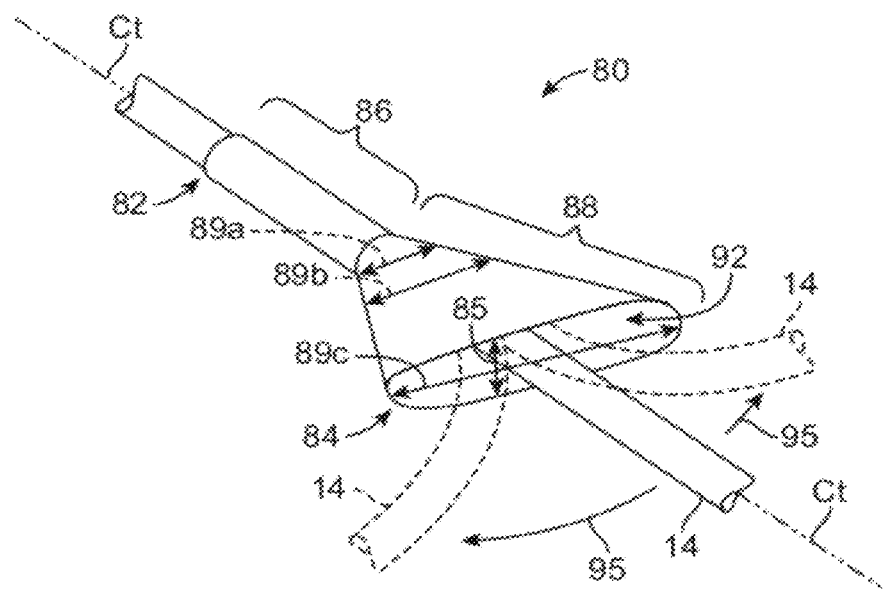
FIGS. 9A and 9B are perspective and sectional views, respectively, showing different tubular devices having non-symmetrical construction.

In other embodiments, as shown in FIG. 9A, a second tube segment 88 of a tubular device 80 is not symmetrical in all radial directions and is somewhat flattened such that the second opening 84 is elongated or oval. In this embodiment, the size of the exit site at the second opening is minimized while still allowing space for the percutaneous cable to bend in radial directions 95 within the second tube lumen 92. The somewhat flattened second tube segment 88 does not form a circular cross section and, thus, has no internal diameter per se. Rather, the flattened second tube segment has one internal cross-dimension 89c which is the maximum dimension in a radial cross-section of the second tube segment and is the maximum range of movement of the cable 14 in the radial direction 95 allowed. The flattened second tube segment has another internal cross-dimension 85 similar to the outer diameter of the cable 14, is orthogonal to internal cross-dimension 89c, and effectively restricts movement of the cable in one plane defined by movement 95.

In FIG. 9A, the cross-dimension 89 enlarges (from 89a to 89c) with distance from the first tube segment 86 that gradually increases like a funnel. At the second opening 84, the cross-dimension is at least twice the diameter of the percutaneous cable. In the embodiment of FIG. 8A wherein the second opening 84 is round, the cross-dimension of the second tube segment 88 corresponds to the internal diameter 81 between any two opposite points along the circumference or perimeter of the opening 84.

Figure 9B:
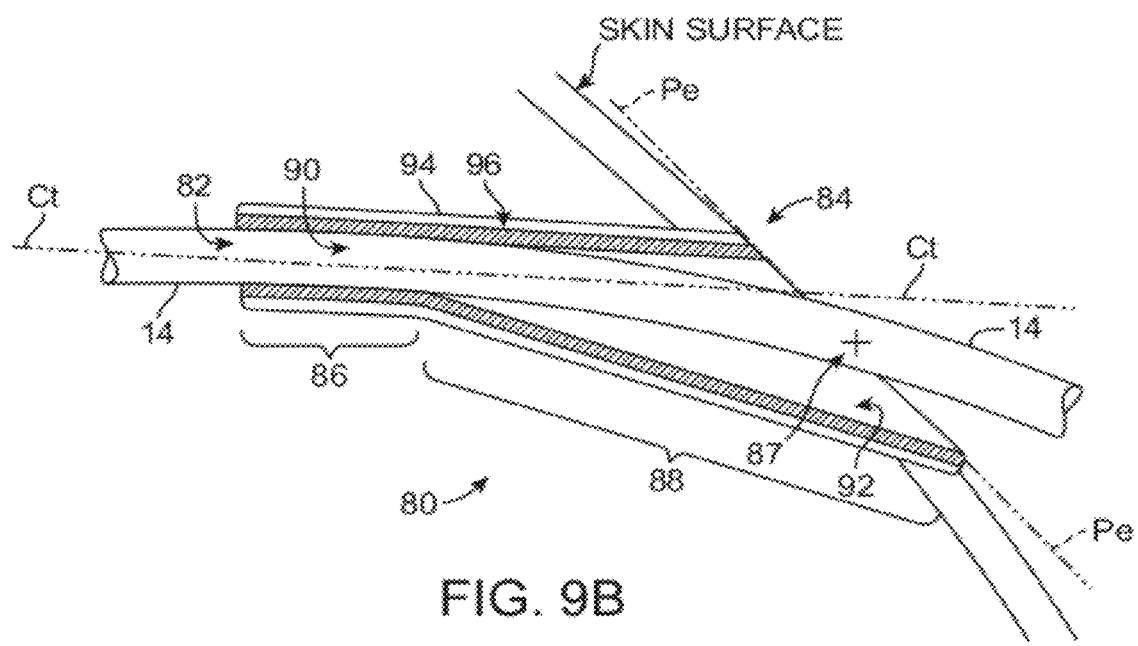

In other embodiments, as shown in FIG. 9B, a second tube segment 88 of a tubular device 80 is biased in a radial direction such that the second opening 84 is off center. That is, the center 87 of the second opening is radially offset (i.e., located at a radial distance away) from a central axis Ct of the first tube segment 86. Also, a plane Pe formed by the edge of the second opening (at the surface of the skin at the exit site) is canted or oriented at an oblique angle from the central axis Ct. With this biased construction for the tubular device, the edge of the second opening can be substantially flush with the skin surface when it is desired to have the percutaneous cable 14 pass at an oblique angle through the exit site.

For the embodiments of FIGS. 8A-9B, the securement device (for attaching the percutaneous cable 14 to tissue) is the porous layer 94 exclusively. There are no sutures or subdermal anchors needed. In other embodiments having a tubular device 80, additional securement can be in the form of sutures that loop through the porous layer 94 near the edge of the second opening 84 and through the skin. In further embodiments, a base piece can be implemented, such as shown in FIGS. 7A and 7B, so that the sutures loop through the tubular device 80 and the base piece without piercing through the skin.

In still other embodiments having a tubular device 80, additional securement of the percutaneous cable can be in the form of a subdermal anchor, such as described below in connection with FIGS. 10A, 14A and 18A. The subdermal anchor is connected to the outer surface 96 of the tubular device and extends radially outward below the skin surface. A porous outer layer 94 of the tubular device and the subdermal anchor work together to secure the percutaneous cable to tissue.

As described below in connection with FIGS. 10A-18B, a percutaneous cable 14 can have attached to it a subdermal anchor configured for implantation within biological tissue surrounding an exit site. The subdermal anchor is attached to and extends radially away from the percutaneous cable, and is designed for attaching to one or more subdermal layers under the skin. In some embodiments, the subdermal anchor is a porous device configured to allow ingrowth of the biological tissue surrounding or in the vicinity of the exit site. In other embodiments, the subdermal anchor is substantially non-porous and comprises barbs or hooks configured to engage surrounding tissue. A subdermal anchor, such as a skirt, can be implanted in a subdermal pocket made in advance by an incision into the biological tissue surrounding the exit wound. In some embodiments, a subdermal pocket is not made ahead of time and a subdermal anchor, such as a filament bundle or barbed filament, is sutured against the surrounding tissue using a needle.

Figure 10A:
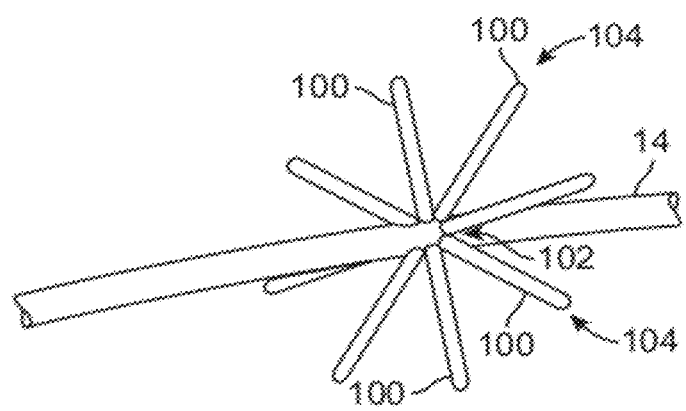
FIGS. 10A-10C are perspective views of subdermal anchors in the form of filament bundles attached to a percutaneous cable.
Figure 10B:
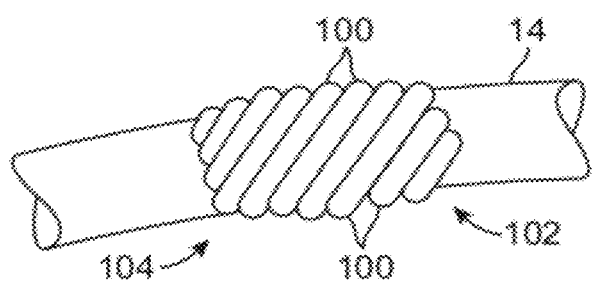

In FIG. 10A, a percutaneous cable 14 has a plurality of subdermal anchors in the form of filament bundles 100 attached to and extending radially away from the percutaneous cable like spokes on a hub. The bundles are flexible. Each bundle has two opposite ends: a fixed end 102, which is located closest to the percutaneous cable; and a free end 104, which is free to move in any direction relative to the percutaneous cable. In FIG. 10A, the bundles are shown in a deployed configuration. In this configuration the bundles are spaced apart from each other such as would occur when implanted below the skin surface. In FIG. 10B, the same bundles are shown in a collapsed configuration, wound tightly around the percutaneous cable, to facilitate axial movement of the percutaneous cable through the tissue and/or skin during a tunneling procedure described further below (for example, such as before the bundles are deployed or during delivery of the cable and device).

Figure 10C:
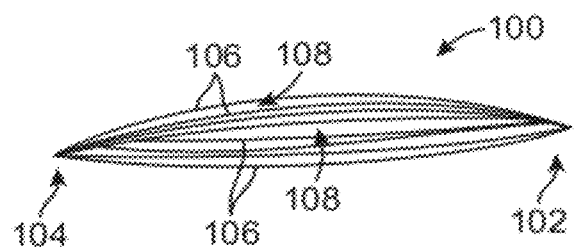

As shown in FIG. 10C, each bundle 100 comprises a plurality of polyester (PET) filaments 106. The total number of filaments in all the bundles can range from about one hundred to thousands. For example, there may be over a hundred filaments per bundle and over ten bundles. Each filament is ultrafine, having a diameter less than 50 microns. In a presently preferred embodiment, each filament is about 12 microns in diameter, ranges from about 2 cm to about 5 cm in length, and has no barbs. The applicant has found that a bundle having more than one hundred filaments with these dimensions functions effectively as a subdermal anchor.

In some embodiments, there is only one filament bundle attached to a percutaneous cable. In other embodiments, the total number of filament bundles attached to a percutaneous cable ranges from 2 to 20, more narrowly from 3 to 15, and more narrowly from 4 to 10.

Within each bundle 100, the filaments 106 are connected to each other at the fixed end 102 and the free end 104 of the bundle. Segments of each filament between the fixed and free ends are free to move away from the other filaments. Gaps 108 or other spaced configuration such as pores between the filaments allow for growth of biological tissue after the bundles are implanted below the skin surface. The result is tissue ingrowth that includes tissue adhesion to and encapsulation of individual filaments. Tissue ingrowth anchors the bundles in place beneath the skin, and the bundles in turn stabilize the percutaneous cable. Thus, tissue surrounding the exit site and the percutaneous cable will move together when the cable and/or skin are jostled, thereby preventing formation of an interfacial gap between the cable and the surrounding tissue. Growth of tissue over the percutaneous cable helps to distribute external forces evenly to the tissue surrounding the percutaneous cable and also reduces the amount of trauma to skin and/or tissue.

Each filament bundle 100 is configured to bend with the skin in which it is embedded. The filament bundle 100 has sufficient flexibility that allows it to move with the skin which has grown into and attached to it. The ability of the filament bundle 100 to flex and move with the skin allows the filament bundle 100 to better maintain a connection to the skin as compared to other subdermal anchors that are rigid. In some embodiments, the filament bundle 100 has a level of compliance that allows it to readily deform with the skin, and has a low resiliency. As used herein, "compliance" is a tendency to yield with the application of an external force, and "resiliency" is a tendency to return to a previous orientation or shape after removal of the external force.

In FIGS. 10A-10C there are eight bundles 100, and the filaments 106 are not woven or braided together. It will be appreciated that one, two, three, or any other number of bundles may be used to stabilize the percutaneous cable. In other embodiments, the filaments of each bundle are braided or twisted together. Individual filaments can also be twisted ribbons with a radial cross-section that is substantially flat as opposed to circular. The filaments can also be in the form of a coil or helix. Twisted, coiled, and helical configurations for the filaments are expected to provide enhanced engagement with surrounding tissue.

Figure 13:
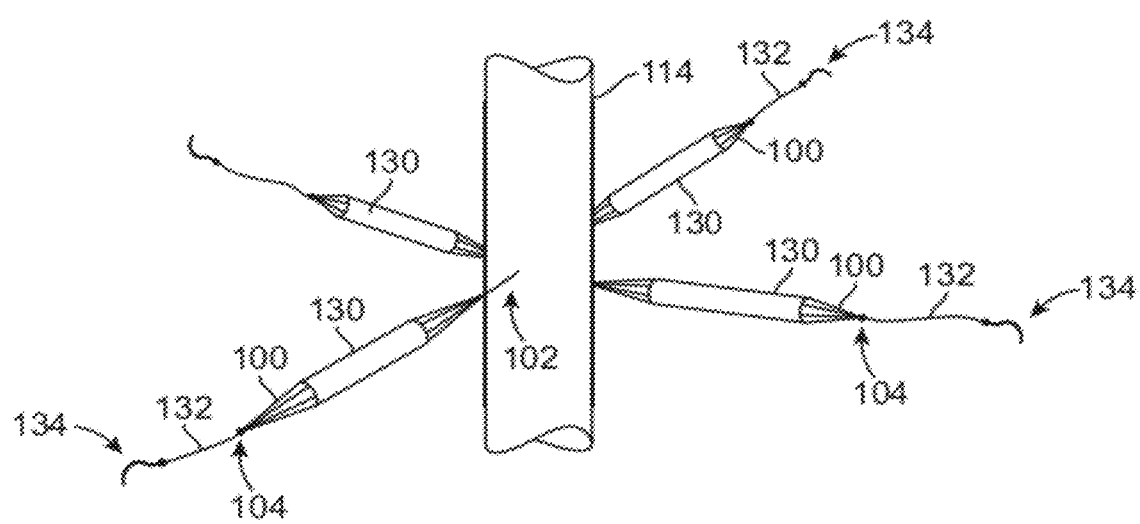
FIG. 13 is a perspective view of a percutaneous cable, showing filament bundles covered by a sheath and connected to sutures and needles.

In FIGS. 10A-10C there is no internal support structure for the bundles 100. In other embodiments, each bundle includes a support structure within or among the polymer filaments. Suitable support structures include a mesh of nickel-titanium alloy strands. The mesh support structure can be collapsed with a sheath 130 (FIG. 13). Upon removal of the sheath, the support mesh opens up, increasing the contact area for tissue adhesion and encapsulation of the filaments 106.

In use, the percutaneous cable 14 is fed through an exit site of the patient and the filament bundles 100 are pulled or pushed into a subdermal pocket around the exit site. The subdermal pocket can be made before or after the percutaneous cable is fed through the exit site.

Figure 11A:
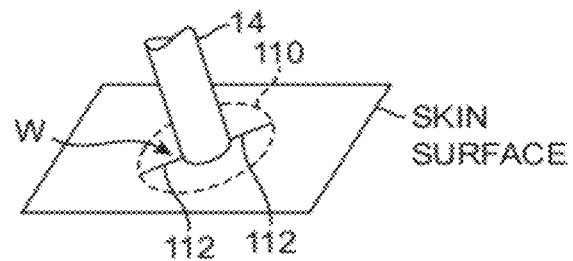
FIGS. 11A-11C are perspective views of different exit sites for a percutaneous cable, showing subdermal pockets formed by different incision methods.
Figure 11B:
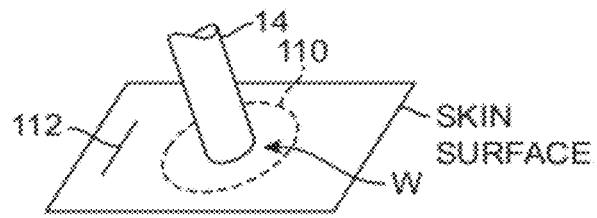
Figure 11C:
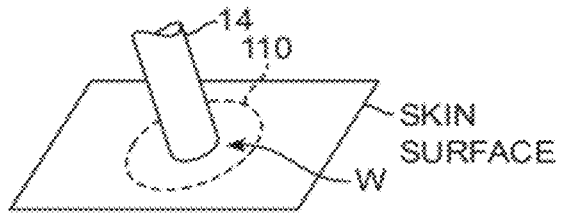

As shown in FIGS. 11A-11C, a subdermal pocket 110 adjacent an exit site W can be made with an incision 112, which can be visible from the surface of the skin (FIGS. 11A and 11B). The outer boundary of the subdermal pocket is illustrated with a broken line to indicate that it is located below the skin surface. The plane in which the subdermal pocket is located, referred to as the subdermal plane, is located below the skin surface and above adipose tissue. The incision 112 can be made to accommodate any size subdermal anchor, including the skirt 140 described further below in connection with FIGS. 14A, 16A, and 17. In other embodiments, a subdermal pocket is made by advancing a needle, which is attached to the bundles 100, through tissue below the skin surface after the percutaneous cable has been fed through the exit site.

Figure 12:
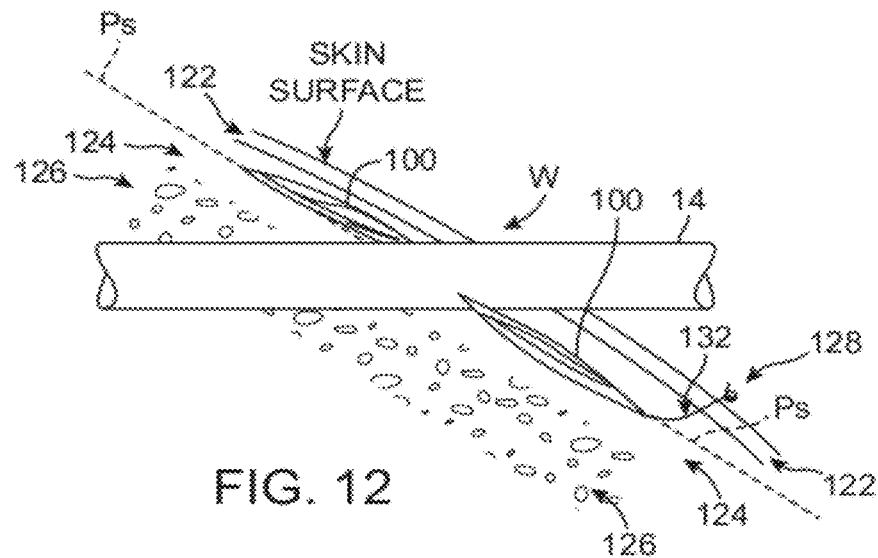
FIG. 12 is a sectional view of an exit site for a percutaneous cable, showing filament bundles within a subdermal pocket located at a subdermal plane above adipose tissue.

As shown in FIG. 12, depending on the angle at which the percutaneous cable 14 exits the skin surface, a subdermal plane Ps and the bundles 100 implanted within it may be at an oblique angle to the percutaneous cable, as opposed to being substantially perpendicular, for example, to minimize protrusion of the cable and to minimize interference of the cable. In FIG. 12, the subdermal plane is within the dermis 124, which is below the epidermis 122 and above the adipose tissue 126. Also, a suture 132 is optionally connected to one of the bundles and is tied in a knot 128 above the skin to provide additional anchoring that prevents the implanted bundle from slipping before tissue grows into the filaments. The knot maintains positioning until tissue ingrowth occurs.

In other embodiments, as shown in FIG. 13, each bundle 100 can be encased within a removable sheath 130 which compresses the filaments together so as to minimize the thickness of the bundle while the percutaneous cable 14 is being moved through an exit site. The sheath can be a plastic tube and can be pulled off of the bundle before or after the bundle is in position within a subdermal pocket. Upon removal of the sheath, individual filaments of the bundle will tend to separate from each other to allow tissue ingrowth. The sheath does not cover the entire bundle. In other embodiments the sheath covers the entire bundle. The sheath may also function to provide some rigidity and to drive the bundles into the surrounding tissue during the initial delivery and placement of the cable and bundles. In alternative embodiments, the sheath is replaced by a trocar inserted from outside of the skin through the subdermal space to allow the fiber bundle to pass through.

Referring again to FIG. 13, the free end 104 of each filament bundle 100 is attached to a suture 132 that is used to pull the bundle into a subdermal pocket. The sutures can be bioabsorbable or non-bioabsorbable. The leading end of the suture may be connected to a needle 134 to help with implantation of the bundle. The sutures can be pulled out through the skin surface and cut away so that none of it remains above the skin surface after the bundles are implanted.

Tissue ingrowth is expected to take one to two weeks after implantation of the bundle. As such, it may be desirable to have a mechanical anchor structure attached to the bundle during the initial one to two week period following implantation. For example, each suture 132 can be tied in a knot individually above the skin surface after the bundle is in place within the subdermal pocket, such as shown in FIG. 12. The knot is sized large enough so that it resists being pulled into the skin and, thus, functions as a mechanical anchor structure before tissue has grown into the bundle. Also, sutures for two or more bundles can be tied together above the skin surface. The resulting looped interconnection above the skin also functions as a mechanical anchor structure which prevents the interconnected bundles from slipping before tissue has grown into the bundle.

It will be appreciated that the bundles 100 need not be in tension after implantation and no rigidity is needed to achieve stabilization of the percutaneous cable after tissue ingrowth. The lack of rigidity of the bundles also makes it easier to perform tunneling of the percutaneous cable through the exit site and implantation of the bundles.

The fixed ends 102 of the bundles 100 can be permanently attached to the percutaneous cable 14 so as to be at the same location on the cable while the cable is being fed through an exit site and while the bundles are manipulated for implantation beneath the skin surface. The fixed ends of the bundles can be fixed in place using any one or a combination of methods, including without limitation, adhesive bonding, heat bonding, tying, and looping through a porous, fabric outer covering of the percutaneous cable. During a tunneling procedure, for example, the ex vivo end of the percutaneous cable is moved through skin from below the skin surface with the fixed ends of the bundles permanently attached in place. Before starting the tunneling procedure, each bundle can be wound, coiled or wrapped tightly around the percutaneous cable, as shown in FIG. 10B, to facilitate movement into the exit site during the tunneling procedure. A temporary wrapper can be placed around the bundles to keep them pressed against the percutaneous cable and thereby facilitate movement into the exit site during the tunneling procedure. The wrapper is subsequently removed to allow the bundles to be implanted beneath the skin.

Since the length of percutaneous cable that is needed to be inside the human body can vary from patient to patient, it may be desirable to have the fixed ends 102 of the bundles 100 be moveable or slideable on the percutaneous cable. For instance, after a desired length of the percutaneous cable 14 is fed through an exit site, the fixed ends can be moved axially on the percutaneous cable until the bundles are at or near the exit site. To allow such movement, the fixed ends can be attached to a holding device, such as a ring described further below, which is removably or slideably attached to the percutaneous cable.

Referring next to FIG. 14A, a percutaneous cable 14 has a subdermal anchor in the form of porous skirt 140 attached to and extending radially away from the percutaneous cable (for example, extending radially away from the longitudinal length or axis of the cable). The skirt comprises an inner edge 142 attached to the percutaneous cable and an outer edge 144 opposite the inner edge. The skirt is a thin, flexible, and substantially flat material. Suitable materials include without limitation a mesh of titanium wires and a mesh of synthetic polymer monofilament, such as polypropylene filament. Conventional mesh material used for hernia repair may also be used for the skirt. The skirt can have one or more radial slits 146 to facilitate placing the skirt in a folded or collapsed configuration, as shown in FIG. 14B. The gaps within the mesh and the slits allow for better blood supply to the epidermis than if the skirt were non-porous and had no slits.

Folding and collapsing of the skirt 140 can be performed my medical personnel as part of an implantation procedure, or performed before as part of a manufacturing process prior to the implantation procedure.

In a currently preferred embodiment, the skirt is uniform in thickness and stiffness.

The porosity of the skirt 140 allows for tissue ingrowth. Tissue ingrowth includes tissue adhesion to and encapsulation of the skirt 140. The skirt 140 is configured to move and bend with the skin in which it is embedded. The skirt 140 has sufficient flexibility that allows it to move with the skin as the underlying subcutaneous tissue has grown into and attached to it. The ability of the skirt 140 to flex and move with the skin allows it to better maintain a connection to the skin as compared to other subdermal anchors that are rigid. In some embodiments, the skirt 140 has a level of compliance that allows it to readily deform with the skin, and has a low resiliency.

The inner edge 142 of the skirt 140 can be permanently attached to a percutaneous cable 14 so that it is at the same axial location on the cable while the cable is being fed through an exit site and while the skirt is manipulated for implantation in a subdermal pocket. The inner edge can be fixed in place using any one or a combination of methods, including without limitation, adhesive bonding, heat bonding, welding, and mechanical crimping. During a tunneling procedure, for example, the ex vivo end of the percutaneous cable is moved through skin from below the skin surface. Before starting the tunneling procedure, the skirt is collapsed tightly against the percutaneous cable, as shown in FIG. 14B to facilitate movement into the exit site during the tunneling procedure. Thereafter, the skirt is unfurled to allow implantation into a subdermal pocket. A temporary wrapper 141 can be placed around the collapsed skirt to keep the skirt in its collapsed state and thereby facilitate movement into the exit site during the tunneling procedure. The wrapper 141 is subsequently removed to allow the skirt to be unfurled into the subdermal pocket.

The inner edge 142 of the skirt 140 may be moveable so that after the percutaneous cable 14 is fed through an exit site, the inner edge can be moved axially on the percutaneous cable until the skirt is at or near the exit site. To allow such movement, the inner edge of the skirt can be attached to a holding device, such as a ring, which is slideable on or removable from the percutaneous cable. As previously mentioned, the fixed ends of filament bundles 100 (FIGS. 10A and 13) can also be attached to a slideable or removable ring.

All the subdermal anchors described herein (i.e., sleeve 40, skirt 140, filament bundle 100, etc.) can optionally be configured to be removed from (or unattached to) the percutaneous cable 14 to facilitate a tunneling procedure in which the percutaneous cable 14 is passed through the skin. The removability can make it easier to perform a tunneling procedure, as compared to an embodiment in which a subdermal anchor has been permanently attached to the percutaneous cable prior to a tunneling procedure. In embodiments where a subdermal anchor is removable from the percutaneous cable, a tunneling procedure can be performed in which the subdermal anchor is separate and completely detached from the percutaneous cable prior to and during the tunneling procedure. After the tunneling procedure is completed, the subdermal anchor is attached to the percutaneous cable at the desired location and embedded in the skin.

A ring for the subdermal anchor, be it a skirt 140 and/or filament bundle 100, can be configured to have a friction fit on the percutaneous cable. The friction fit can be such that a sliding force must be applied to the ring for there to be any change in axial position on the percutaneous cable. A ring 148 for holding a subdermal anchor can be as shown in FIG. 15A. As shown in FIG. 15B, a percutaneous cable 14 can have a receptacle 152 configured to receive and retain the ring 148. The receptacle comprises a circumferential groove 154 and a plurality of protrusions 156 on the outer surface of the percutaneous cable.

In some embodiments, the skirt 140 is not wrapped around the percutaneous lead during an implantation procedure. During a manufacturing process, the skirt 140 is located outside of the sleeve, then fed into and folded within the sleeve (i.e., within the lumen of the sleeve). The inner edge 142 corresponds to a portion of the skirt 140 which remains outside of the sleeve lumen is welded to the sleeve and the percutaneous lead, or welded to the sleeve and the ring 148 attached to the ring. The ring 148, skirt 140 and sleeve are pre-attached, meaning they are already in place on the percutaneous lead 14 prior the start of an implantation or tunneling procedure. The skirt 140 is configured to bend at the weld junction to allow the skirt 140 to unfurl during implantation. The portion of the skirt 140 at the weld junction can be thicker or have a reinforcement structure attached to it to prevent damage to the skirt 140 at the weld junction.

Figure 16A:
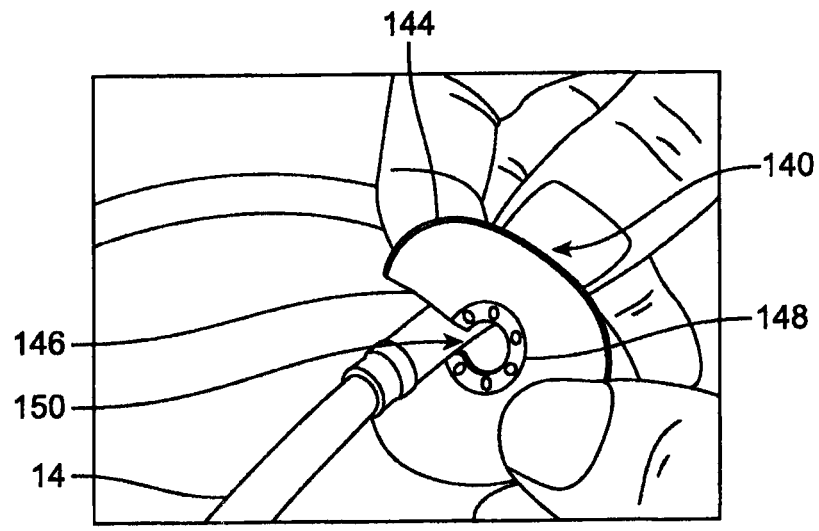
FIGS. 16A and 16B are photographs of a mesh skirt having one slit and attached to a split ring removably attached to a percutaneous cable.
Figure 16B:
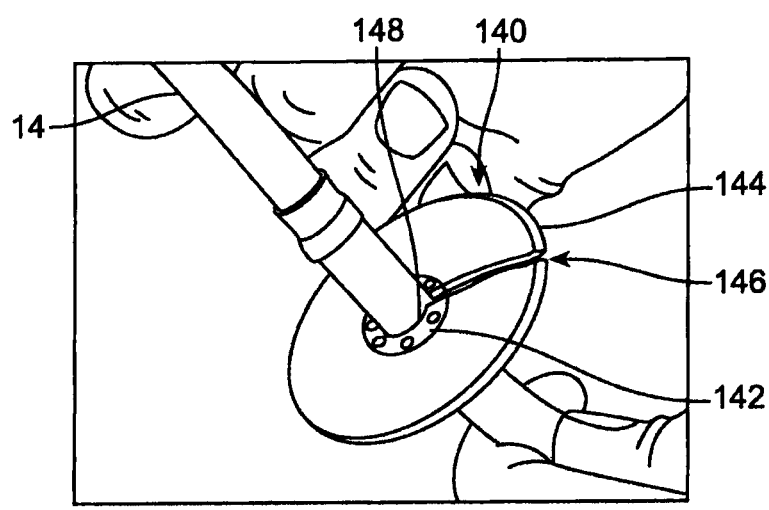

In some embodiments, as shown in FIGS. 16A and 16B, a split ring 148 is attached to an inner edge 142 of the skirt 140. A cut 150 through the split ring corresponds in position to the single slit 146 in the skirt. The cut forms opposite ends on the split ring which are spaced apart from each other by a distance that is smaller than the outer diameter of a percutaneous cable 14. In use, the split ring can be bent, as shown in FIG. 16A, to temporarily spread apart the split ring ends and thereby allow the split ring to be mounted around the percutaneous cable 14 at any axial position on the cable and at any time, before or after the cable has been fed through an exit site. When positioned, as shown in FIG. 16B, the split ring clamps tightly around the percutaneous cable. Clamping can be due to superelastic shape memory of the split ring material. Alternatively, the split ring can be crimped with a tool onto the percutaneous cable to fix it in place. Suitable materials for the split ring include without limitation titanium, titanium alloy, nickel titanium alloy and stainless steel.

Figure 17:
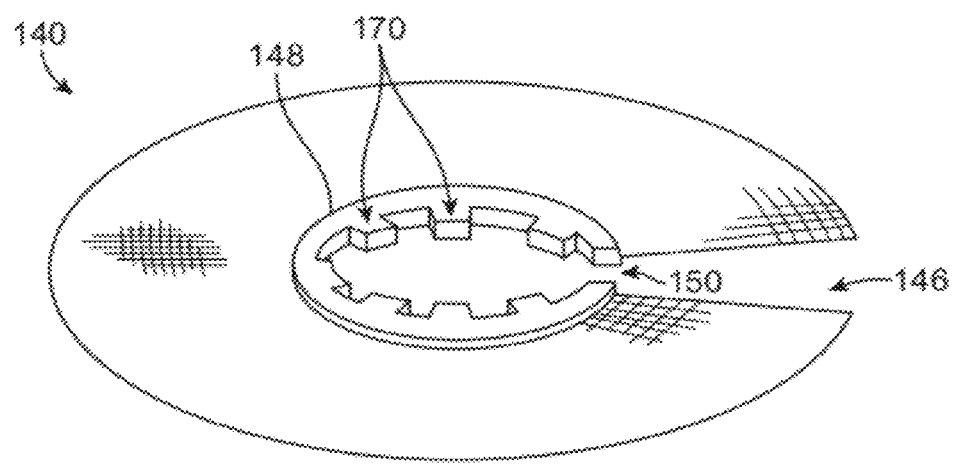
FIG. 17 is a perspective view of a subdermal anchor in the form of a mesh skirt having a single slit, showing a split ring attached to an inner edge of the mesh skirt and showing a cut in the ring corresponding with the slit on the skirt.

In some embodiments, as shown in FIG. 17, a split ring 148 comprises a plurality of teeth 170 that face radially inward. When the split ring is positioned, such as described for FIG. 16B, the teeth clamp down onto the percutaneous cable and prevent axial movement of the split ring. Thereafter, the split ring can be twisted or rotated while on the percutaneous cable to adjust its axial position. Although a mesh skirt 140 is shown attached to the split ring, it will be appreciated that the split ring can be used to attach filament bundles and other types of subdermal anchors.

The angle and number of the teeth 170 of the split ring 148 can control the amount of pulling force needed to be applied to the percutaneous lead 14 that will cause the percutaneous lead 14 to slip relative to the split ring 148. The amount of force which results in slippage is referred to as a break-away force. In FIG. 17, the split ring 148 has seven teeth 170. It should be understood that the split ring 148 can include a lesser or greater number of teeth 170, as desired, to provide for a lesser or greater break-away force. As shown in FIG. 17, the teeth 170 are oriented in-plane, meaning they extend in directions that are in the plane defined by the outer perimeter or circumference of the split ring 148. Alternatively, the teeth 170 can be oriented off-plane, meaning that they are oriented downward or upward so that they extend in directions at an oblique angle to the plane defined by the outer perimeter of the split ring 148. The oblique angle can be selected, as desired, to provide for a lesser or greater break-away force as compared to the in-plane orientation of the teeth 170 shown in FIG. 17.

Other types of subdermal anchors for stabilizing a percutaneous cable include barbed filaments of synthetic polymer. The polymer can be bioabsorbable or non-bioabsorbable. Suitable materials and construction for the barbed filament include those used for conventional barbed surgical sutures.

Figure 18A:
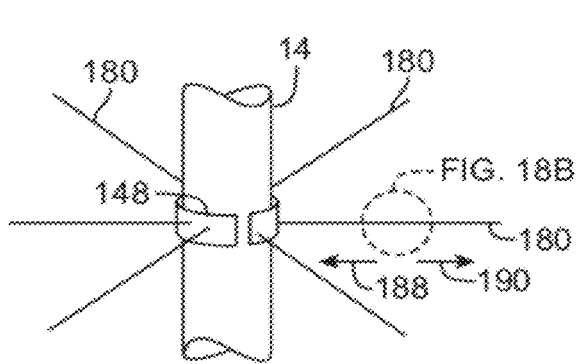
FIGS. 18A and 18B are perspective and sectional views, respectively showing subdermal anchors in the form of barbed filaments attached to a percutaneous cable and showing individual barbs formed by cuts in a filament.
Figure 18B:
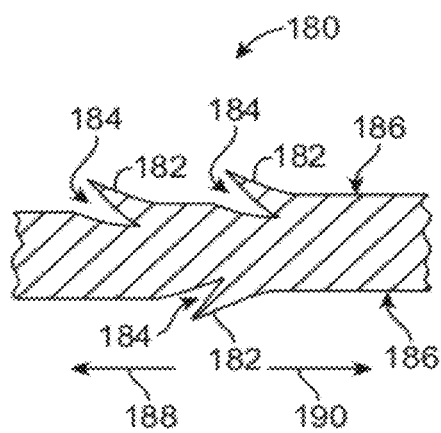

As shown in FIG. 18A, barbed filaments 180 can be attached to a percutaneous cable 14 using a split ring 148. As shown in FIG. 18B, individual barbs 182 can be formed by making cuts 184 at oblique angles into the outer surface 186 of the filament. The barbs are unidirectional in that they inhibit radially inward movement 188 of the filament toward the percutaneous cable yet allow radially outward movement 190 in the opposite direction to allow the filament to be pulled through biological tissue surrounding an exit wound. In other embodiments, no split ring is used and the barbed filaments are attached directly to the percutaneous cable by tying them onto the percutaneous cable and/or hooking them through an outer covering of the percutaneous cable.

Figure 19:
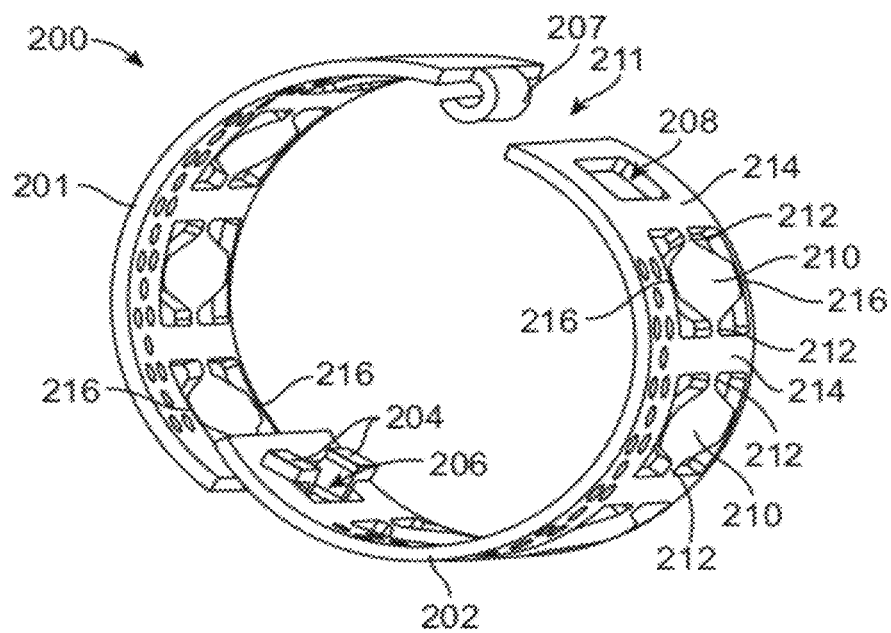
FIGS. 19-22 are perspective views showing different embodiments of a ring for attaching a subdermal anchor to a percutaneous cable.

In some embodiments, as shown in FIG. 19, a ring 200 for securing a subdermal anchor to a percutaneous cable comprises two separate parts, referred to as a first part 201 and a second part 202. The first and second parts are hinged together to allow them to open and close relative to each other. The first part 201 includes two hinge elements 204 that are received into a first hole 206 formed through the second part 202. The hinge elements 204 have hooks that keep the first and second parts 201, 202 connected together while still allowing the first and second parts to open and close by pivoting about the hinge elements. The first part 201 includes a latch element 207 configured to hook into a second hole 208 formed into the second part 202. The latch element 207 and the second hole 208 form a lock device that keeps the first and second parts 201, 202 closed and locked around the percutaneous cable. It will be appreciated that either the latch element or the hinge elements may be disposed on the second part 202 instead of the first part.

The first and second parts 201, 202 each include a plurality of diamond-shaped tangs 210 connected by slender circumferential links 212 to the main body 214 of the first and second parts. Each tang 210 includes two points or peaks 216 which are free to move relative to the main body 214 with the application of force during installation on the percutaneous cable, as will be explained below. The first and second parts 201, 202 include a plurality of small holes to facilitate tissue integration. In other embodiments, first and second parts 201, 202 include other holes, larger than those illustrated in FIG. 19, for attaching a subdermal anchor, such as a mesh skirt, fiber bundle, or barbed filament.

In use, the first and second parts 201, 202 are assembled together as shown in FIG. 19 so that the hinge elements 204 are hooked into the first hole 206, thereby allowing the first and second parts to pivot between open and closed positions. The latch element 207 is unlocked, as shown in FIG. 19. Thereafter, the two parts 201, 202 are spread apart to increase the size of the opening 211 between the two parts such that a percutaneous cable can pass through the opening. After the percutaneous cable is located between the two parts 201, 202, the two parts can be brought back together so that the latch element 207 hooks into the second hole 208. Either before or after the percutaneous cable is placed between the two parts 201, 202, the tangs 210 can be pushed radially inward so that at least one peak of each tang protrudes radially inward from the main body 214 of the two parts 201, 202. The links 212 are configured to twist to allow the tangs 210 to be pushed or bent inward with the application of force to the tangs, and with the removal of force, the tangs remain at their pushed-in position. With the tangs 210 pushed in, the peaks 216 function like teeth that grab, clamp, and/or push into the outer surface of the percutaneous cable.

In some embodiments, the tangs 210 provide the predominant means of attachment to the percutaneous cable, without any need for adhesives or sutures to keep the ring in place on the cable. In other embodiments, the means of attachment includes tangs, adhesives and/or sutures.

Figure 20:
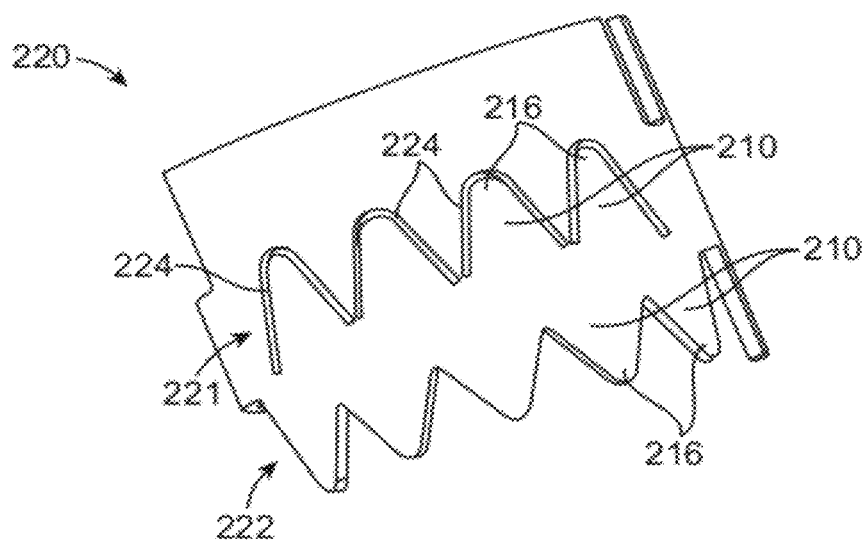
Figure 21:
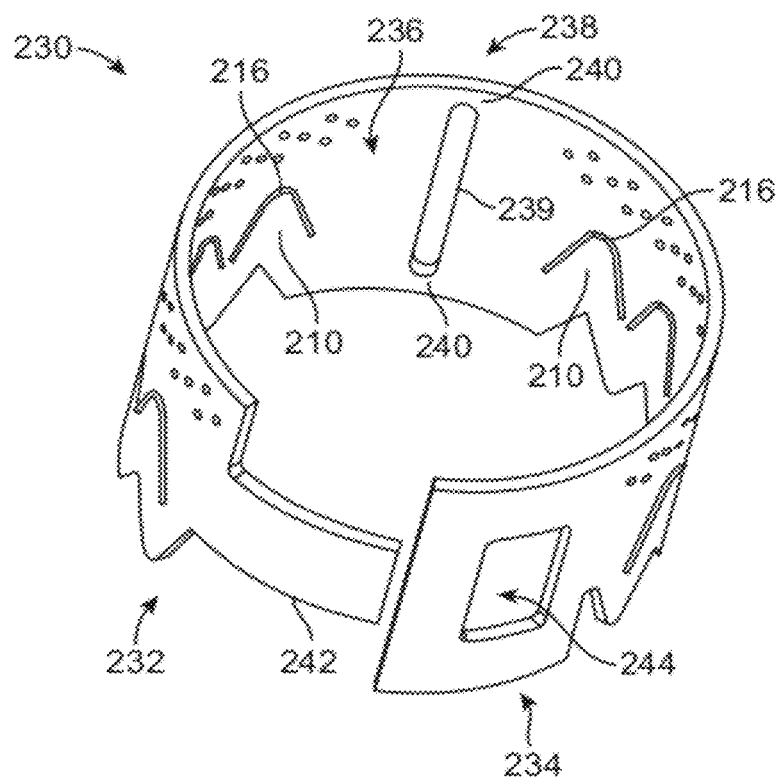
Figure 22:
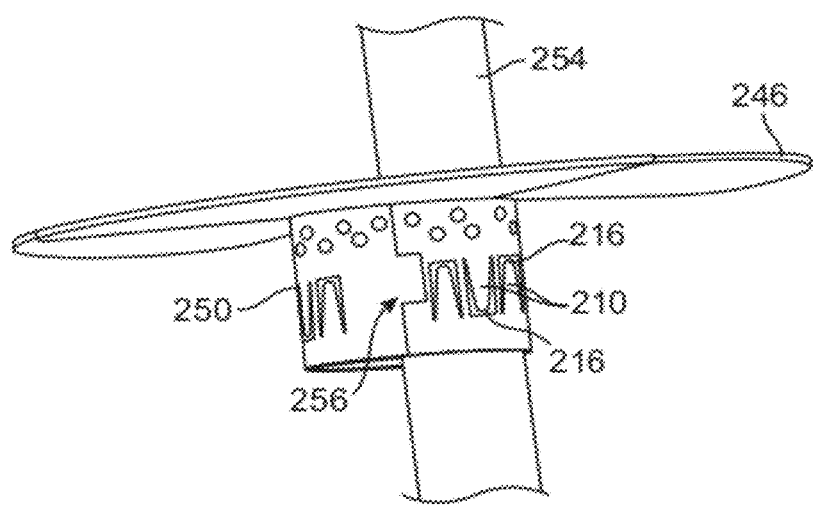

As shown in FIGS. 20-22, various types of rings can have tangs 210 arranged in different ways.

As shown in FIG. 20, a ring 220 includes triangular tangs 210, each tang having only one peak 116. The triangular tangs 210 are arranged in two circumferential rows so that in one row 221 the peaks 216 point in one axial direction and in another row 222 the peaks 216 point in the opposite axial direction. The tangs 210 in the top row 221 are defined by narrow cuts or slits 224 formed through the main body of the ring. By radially bending the peaks 216 which face in the same axial direction, the ring 220 is prevented from slipping in only one axial direction on the percutaneous cable, thereby allowing the axial position of the ring to be adjusted on the percutaneous cable. By radially bending the peaks 216 which face in opposite axial directions, the ring 148 is locked in place and prevented from slipping in both axial directions on the percutaneous cable. It will be appreciated that the ring 220 can include one or any number of circumferential row of triangular tangs and the peaks in the various rows can face in the same or opposite directions.

As shown in FIG. 21, a ring for securing a subdermal anchor to a percutaneous cable can be a one-piece, cylindrical sleeve 230 as opposed to having two separate parts. The sleeve 230 includes two circumferential rows of tangs 210 with peaks 216 of one row facing in an opposite direction to the peaks of the other row. In use, the opposing ends 232, 234 of the sleeve 230 are free to move apart from each other to allow a percutaneous cable to be inserted within the central lumen 236 of the sleeve 230. The sleeve 230 includes a hinge feature 238 configured to make it easier for the ends 232, 234 to move apart and closer together. The hinge feature 238 includes a single axial slot or cut 239 which forms two relatively narrow links 240 that function as a "living" hinge by flexing without breaking. It will be appreciated that other types of hinge features can be implemented such as, for example, a groove, depression, or bend instead of a cut that passes entirely through the sleeve. The opposing ends 232, 234 include mating features 242, 244 configured to interlock with each other and thereby prevent the opposing ends from pulling apart after the percutaneous cable is inserted inside the sleeve.

FIG. 22 shows an alternative embodiment of a ring 250 being used to attach a skirt-type subdermal anchor 246 onto a percutaneous cable 254. The ring 250 has only one row of tangs 210. The tangs 210 are arranged so that peaks 216 alternate in direction, with some peaks pointing up and some peaks pointing down. The ring 250 includes a hinge device 256 that allows the ring 250 to open and close.

Suitable materials for the above-describe rings 148, 200, 220, 230, 250 include, without limitation, titanium, titanium alloy, nickel titanium alloy and stainless steel.

Suitable materials for a subdermal anchor include without limitation polyester, silicone, polypropylene, polyurethane, and titanium. Suitable construction morphology for a subdermal anchor include without limitation velour, foam, mesh, and felt. Any combination of these materials and construction morphologies can be used to form an elongate bundle, skirt, and other subdermal anchor, any of which can be attached to a percutaneous cable 14 in the same manner as described above for the filament bundle 100 and the skirt 140.

While several particular forms of the invention have been illustrated and described, it will also be apparent that various modifications can be made without departing from the scope of the invention. For example, although the above description has been made with frequent reference to a human body, it will be appreciated that a percutaneous cable can be stabilized on an animal body using the described features and aspects of the disclosed embodiments. Also, the above features and aspects of the disclosed embodiments can be used for stabilizing a percutaneous cable or lead for diagnostic or therapeutic medical devices other than a mechanical pump.

It is also contemplated that various combinations or subcombinations of the specific features and aspects of the disclosed embodiments can be combined with or substituted for one another in order to form varying modes of the invention. For example, a percutaneous cable can be stabilized using one or more sutures as described in connection with FIGS. 2-7B in combination with one or more subdermal anchors as described in connection with FIGS. 10A-18B. As a further example, a percutaneous cable can be stabilized using a funnel-like tubular device as described in connection with FIGS. 8A-9A in combination with one or more sutures as described in connection with FIGS. 2-7B and/or one or more subdermal anchors and rings as described in connection with FIGS. 10A-22.

Accordingly, it is not intended that the invention be limited, except as by the appended claims.

What is claimed is:

1. An assembly comprising:
   a percutaneous cable including a power line for powering a mechanical cardiac pump and a communication line for data communication with the mechanical cardiac pump;
   an anchor attached to the percutaneous cable, the anchor comprising a mesh in a collapsed state, the mesh configured to engage biological tissue by tissue growth in the mesh, there being a slit formed through an outer edge of the mesh;
   a split ring connecting the anchor to the percutaneous cable, the split ring configured to slide axially along the percutaneous cable and to clamp onto or be crimped onto a selected position on the percutaneous cable; and
   a wrapper fixedly attached to and disposed around the anchor to keep the anchor in the collapsed state.

2. The assembly of claim 1, wherein the wrapper is removable, and the mesh is configured to be unfurled from the collapsed state to an extended state in which the mesh extends radially away from the percutaneous cable when the wrapper is removed.

3. The assembly of claim 2, wherein the anchor extends radially away from the split ring when in the extended state.

4. The assembly of claim 1, wherein the percutaneous cable comprises a receptacle configured to receive the split ring, the receptacle having a groove in which the split ring can be received to inhibit axial movement of the split ring relative to the percutaneous cable.

5. The assembly of claim 1, wherein the split ring comprises a plurality of teeth engaging and protruding radially inward toward the percutaneous cable.

6. The assembly of claim 1, further comprising a mechanical cardiac pump connected to the percutaneous cable.

7. The assembly of claim 1, wherein the percutaneous cable comprises an electrical connector configured to selectively engage and disengage from another electrical connector.

8. The assembly of claim 1, wherein a cut is formed through the split ring, and the cut forms opposite ends of the split ring which are spaced apart from each other by a distance that is smaller than an outer diameter of the percutaneous cable.

9. The assembly of claim 8, wherein the split ring is configured to bend in order to temporarily spread apart the opposite ends of the split ring.

10. The assembly of claim 1, wherein the split ring is configured to clamp onto the percutaneous cable.

11. The assembly of claim 10, wherein the split ring is configured to clamp onto the percutaneous cable due to elasticity of the split ring.

12. The assembly of claim 1, wherein the split ring is configured to be crimped onto the percutaneous cable to fix the split ring in place on the percutaneous cable.

13. The assembly of claim 1, wherein the slit extends from an inner edge of the mesh to the outer edge of the mesh.

14. The assembly of claim 1, wherein the slit forms a gap between portions of the mesh that are adjacent to the slit.

15. An assembly comprising:
   a percutaneous cable including a power line for powering a mechanical cardiac pump and a communication line for data communication with the mechanical cardiac pump;
   an anchor attached to the percutaneous cable, the anchor configured to slide axially along the percutaneous cable, the anchor comprising a mesh configured to engage biological tissue by tissue growth in the mesh; and
   a wrapper fixedly attached to and disposed around the anchor to keep the anchor in a collapsed state until the wrapper is removed from the anchor,
   wherein one or more slits are formed through an outer edge of the mesh, and the mesh is configured to be unfurled from the collapsed state to an extended state in which the mesh extends radially away from the percutaneous cable.

16. The assembly of claim 15, further comprising a mechanical cardiac pump connected to the percutaneous cable.

17. The assembly of claim 15, wherein each slit extends radially outward from an inner edge of the mesh to the outer edge of the mesh.

18. The assembly of claim 15, wherein each slit forms a gap between portions of the mesh that are adjacent to the slit.

* * * * *